United States Patent
Fukuda et al.

[11] Patent Number: 4,772,681
[45] Date of Patent: Sep. 20, 1988

[54] PORPHYRIN DERIVATIVES

[75] Inventors: Yozo Fukuda, Toyonaka; Takuzo Otani, Wako; Haruo Yamada, Nara; Michikazu Sawada, Kyoto; Katsuo Aizawa, Yokohama; Mari Uchimoto, Higashiosaka; Michito Karasawa, Nagaoka, all of Japan

[73] Assignee: Hamari Chemicals, Ltd., Osaka, Japan

[21] Appl. No.: 4,333

[22] Filed: Jan. 15, 1987

[30] Foreign Application Priority Data

Jan. 17, 1986 [JP] Japan .................................. 61-8789
Mar. 3, 1986 [JP] Japan .................................. 61-46000
Dec. 8, 1986 [JP] Japan .................................. 61-291904

[51] Int. Cl.$^4$ .......................................... C07D 487/22
[52] U.S. Cl. .......................................... 540/145; 424/9
[58] Field of Search .......................................... 540/145

[56] References Cited
U.S. PATENT DOCUMENTS

| | | | |
|---|---|---|---|
| 4,604,241 | 8/1986 | Sakata et al. .................. | 540/145 |
| 4,634,557 | 1/1987 | Sato .................................. | 540/145 |
| 4,649,151 | 3/1987 | Dougherty et al. .............. | 540/145 X |
| 4,656,186 | 4/1987 | Bommer et al. .................. | 540/145 X |
| 4,675,338 | 6/1987 | Bommer et al. .................. | 540/145 X |

Primary Examiner—Richard L. Raymond
Attorney, Agent, or Firm—Burgess, Ryan and Wayne

[57] ABSTRACT

Novel porphyrin derivatives of the general formula:

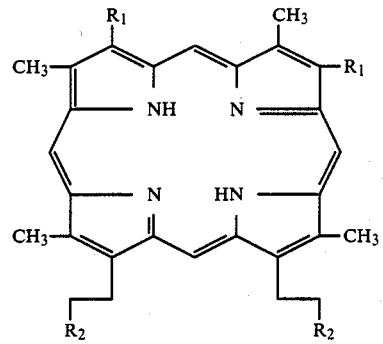

wherein $R_1$ each independently denotes a hydrogen, a $C_1$-$C_4$ alkyl group or an ethenyl group, and $R_2$ each independently denotes $COZ(C_mH_{2m})Q$, $COZCH(C_mH_{2m}Q)_2$, $-CH_2-Q$ [wherein Z is O, S or NH, m is an integer of 1 to 23, and Q is a di-($C_1$-$C_4$ alkyl)amino group or tri-($C_1$-$C_4$ alkyl)ammonium halide group] or

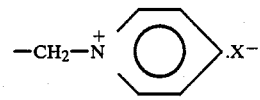

(wherein X is a halogen); or $R_1$ each independently denotes $-C_2H_4-Q$ (wherein Q is the same as defined above),

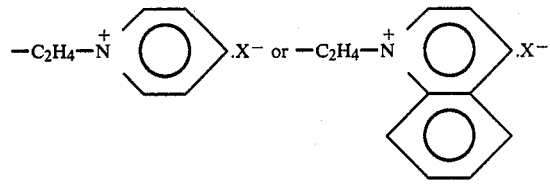

(wherein X is the same as defined above), and $R_2$ each independently denotes a carboxyl group or a $C_1$-$C_4$ alkoxycarbonyl group, and the production thereof are described. The quarternary ammonium salt type of the above compounds exhibit affinity and photosensitizing activity for cancer cells and can be employed for diagnosing and treating cancer under irradiation of laser light.

7 Claims, No Drawings

PORPHYRIN DERIVATIVES

FIELD OF THE INVENTION

This invention relates to novel porphyrin derivatives which are utilizable for the diagnosis and treatment of cancer.

BACKGROUND OF THE INVENTION

In recent years, the porphyrin derivatives exhibiting photosensitizing activity and affinity for cancer cells when employed in conjunction with irradiation of laser light, can increasingly produce excellent results in the diagnosis and treatment of cancer (T. J. Dougherty, "Porphyrin Localization and Treatment of Tumors", pp. 75–78 (1984)]. For this purpose, frequently use is made mainly of hematoporphyrin or hematoporphyrin derivative. However, the former compound is difficult to be obtained in the pure state [R. K. DiNello et al., "The Porphyrins", vol. 1, pp. 297–298 (1978)]., whereas the latter is produced by acetylating the former, followed by treatment with alkali and acid and consists of a mixture of several kinds of porphyrin derivatives. Accordingly, such porphyrins are considered to present significant problems in clinical application.

At present, the hematoporphyrin derivative, the utilization of which is being tried in the diagnosis and treatment of cancer, is obtainable only in a mixture of several kinds of different compounds as mentioned in the above. This renders it quite difficult to obtain the compound of invariably constant quality and consequently constitutes great difficulty in conducting tests on the efficacy or toxicity and the like. In order to solve such problem, it is considered important to obtain the pure porphyrin derivative that can demonstrate both photosensitizing activity and affinity for cancer cells.

SUMMARY OF THE INVENTION

The present inventors synthesized various kinds of porphyrin derivatives exhibiting phtosensitizing activity and affinity for cancer cells by chemical modification of the propionic acid groups at the 2- and 18-positions, or ethenyl groups at 7- and 12-positions of porphyrin represented by the general formula;

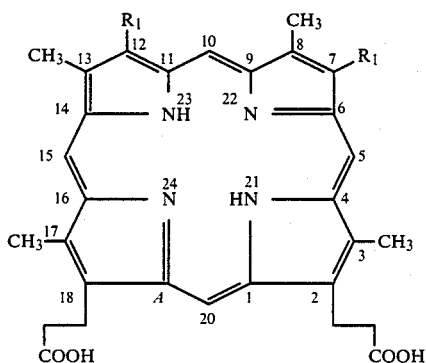

(wherein $R_1$ is a hydrogen, a $C_1$–$C_4$ alkyl group or an ethenyl group).

This invention is directed to a porphyrin derivative represented by the general formula:

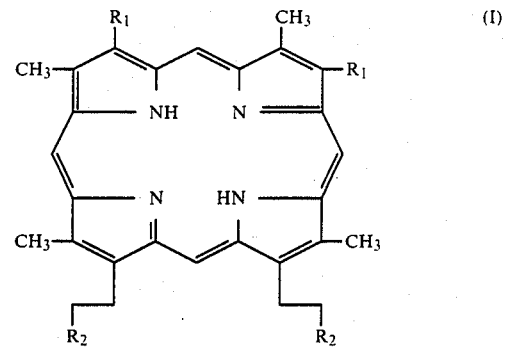

wherein $R_1$ each independently denotes a hydrogen, a $C_1$–$C_4$ alkyl group or an ethenyl group, and $R_2$ each independently denotes $COZ(C_mH_{2m})Q$, $COZCH(C_mH_{2m}Q)_2$, —$CH_2$—Q [wherein Z is O, S or NH, m is an integer of 1 to 23, and Q is a di-($C_1$–$C_4$ alkyl)amino group or tri-($C_1$–$C_4$ alkyl)ammonium halide group] or

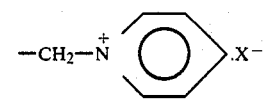

(wherein X is a halogen); or $R_1$ each independently denotes —$C_2H_4$—Q (wherein Q is the same as defined above),

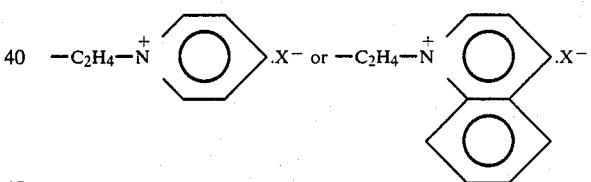

(wherein X is the same as defined above), and R each independently denotes a carboxyl group or a $C_1$–$C_4$ alkoxycarbonyl group.

$C_1$–$C_4$ alkyl group denoted by $R_1$ in the formula (I), $C_1$–$C_4$ alkyl in di-($C_1$–$C_4$ alkyl)amino group or tri ($C_1$–$C_4$ alkyl)ammonium halide group included in the definition of Q, or $C_1$–$C_4$ alkyl in $C_1$–$C_4$ alkoxycarbonyl group denoted by $R_2$ in the formula (I) is an alkyl group such as methyl, ethyl, propyl or butyl. $C_3$–$C_4$ alkyl group may be a straight or branched chain.

DETAILED DESCRIPTION OF THE INVENTION

The embodiments of the porphyrin derivative (I) can be illustratd by the formulas (III), (IV) and (VI) described below:

One group of porphyrin derivatives (I) can be represented by the following formula;

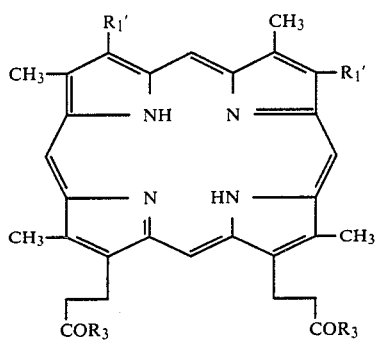

(III)

(wherein $R_1'$ is a hydrogen, a $C_1$-$C_4$ alkyl group or an ethenyl group; $R_3$ is $O(C_mH_{2m})N(R)_2$, $OCH(CH_2N(R)_2)_2$, $S(C_mH_{2m})N(R)_2$, $NH(C_mH_{2m})N(R)_2$, $O(C_mH_{2m})N^+(R)_3 \cdot X^-$, $OCH(CH_2N^+(R)_3)_2 \cdot 2X^-$, $S(C_mH_{2m})N^+(R)_3 \cdot X^-$ or $NH(C_mH_{2m})N^+(R)_3 \cdot X^-$ (wherein R is a $C_1$-$C_4$ alkyl group; X is a halogen; m is an integer of 1 to 23; n is an integer of 1 to 4).

Referring to the formula, R is $C_1$ to $C_4$ alkyl, such as methyl or ethyl, or straight or branched propyl or butyl.

By halogenating porphyrin of the general formula (II) and conducting a condensation reaction of the resulting acid halide with a compound represented by the formula $HO(C_mH_{2m})N(R)_2$, $HOCH(CH_2N(R)_2)_2$, $HS(C_mH_{2m})N(R)_2$ or $H_2N(C_mH_{2m})N(R)_2$ (wherein R, m and n are as defined hereinbefore) or its salt in a solvent in the presence or absence of an acid-capturing agent, there are obtained the porphyrin derivatives of the formula (III) wherein $R_2$ is $O(C_mH_{2m})N(R)_2$, $OCH(CH_2N(R)_2)_2$, $S(C_mH_{2m})N(R)_2$ or $NH(C_mH_{2m})N(R)_2$.

As the solvent employed in this condensation reaction, there may be mentioned methylene chloride, chloroform, ethyl acetate, etc., with methylene chloride normally being preferentially employed. Examples of the acid-capturing agent include triethylamine, pyridine, quinoline and the like, with triethylamine being preferably used. The reaction temperature and reaction time can be suitably selected. Ordinarily, the reaction is completed at 0° C. for 0.5 to 5 hours. When methylene chloride is used as a solvent, for example, the condensation reaction can be completed at a temperature maintained at the refluxing temperature of methylene chloride for 1 to 2 hours. The porphyrin derivatives of the formula (III) where $R_3$ is $O(C_mH_{2m})N^+(R)_3 \cdot X^-$, $OHC(CH_2N^+(R)_3)_2 \cdot 2X^-$, $S(C_m H_{2m})N^+(R)_3 \cdot X^-$ or $NH(C_mH_{2m})N^+(R)_3 \cdot X^-$ can be obtained by the following procedure;

The porphyrin derivative of the formula (III) wherein $R_3$ is $O(C_mH_{2m})N(R)_2$, $OCH(CH_2N(R)_2)_2$, $S(C_mH_{2m})N(R)_2$ or $NH(C_mH_{2m})N(R)_2$ is reacted with a lower alkyl halide in the presence or absence of a solvent to convert to its quaternary ammonium salt. As the preferred solvent which is used in this reaction, there may be mentioned methylene chloride, chloroform, ethylene dichloride, etc. The reaction temperature and reaction time can be suitably selected. For example, the reaction is completed at 0° C. to 100° C. for 5 minutes to 5 hours, but the reaction can normally be concluded at 20° C. to 30° C. for 0.5 to 1 hour.

Another group of the present porphyrin derivatives (I) can be represented by the formula;

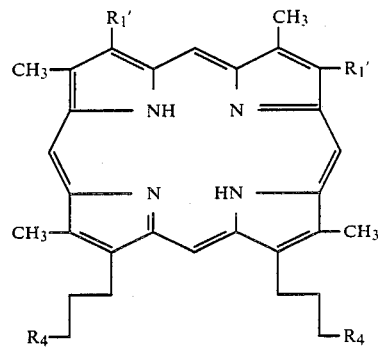

(IV)

[wherein $R_1'$ is the same as defined above and $R_4$ is $N^+(R)_3 \cdot X^-$ (wherein R is a $C_1$-$C_4$ alkyl group and X is a halogen) or pyridinium halide group]. The porphyrin derivative (IV) can be obtained by halogenating a porphyrin derivative of the formula,

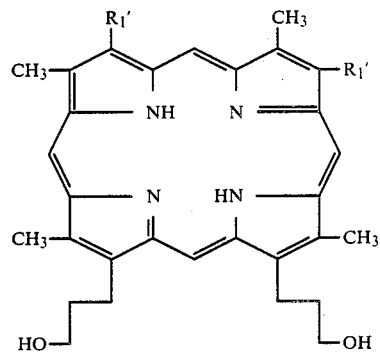

(V)

to convert respective OH groups in the above formula to halogens and reacting the halogenated compound with a tertiary amine.

The halogenation may be carried out by reacting a porphyrin derivative of the formula (V) with a halogenating agent in the presence of a solvent. As the halogenating agent which is utilizable in the reaction, there may be mentioned thionyl halides, hydrogen halides, etc., while the solvent includes, for example, methylene chloride, chloroform, pyridine and the like. The reaction may normally be completed at 0° to 80° C. for 1 to 5 hours. When thionyl bromide is used as a halogenating agent, however, the reaction is ordinarily completed at 20° to 30° C. for 3 to 5 hours.

The halogenated derivative thus obtained is rejected with a corresponding tertiary amine in the presence or absence of a solvent. As the solvent employable in the reaction, there may be mentioned methylene chloride, chloroform, ethylene dichloride, etc. The reaction may normally be completed at 0° to 100° C. for 5 minutes to 5 hours. When pyridine is used as an amine, for example, the reaction is normally completed by refluxing the mixture of the halogenated derivative with pyridine for 1 to 3 hours.

A further group of the present porphyrin derivative can be represented by the formula;

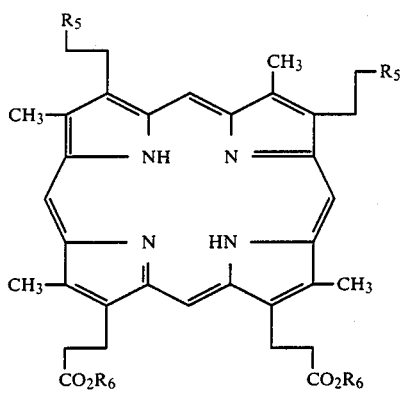

(VI)

[wherein $R_5$ is $N^+(R)_3 \cdot X^-$ (wherein R is a $C_1-C_4$ alkyl group and X is a halogen), pyridinium halide group or quinolinium halide group; and $R_6$ is a hydrogen or a $C_1-C_4$ alkyl group].

The derivative (VI) can be obtained by reacting a porphyrin derivative of the formula;

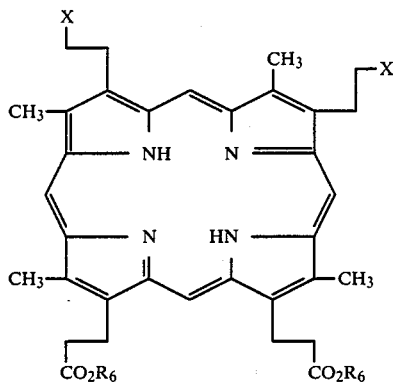

(VII)

(wherein $R_6$ and X are the same as defined above) with a corresponding tertiary amine.

The $C_1-C_4$ alkyl groups each denoted by $R_6$ or by R in $N^+(R)_3 \cdot X^-$ which is included in the definition of $R_5$ is independently an alkyl group such as methyl or ethyl, or propyl or butyl which may branches.

As pyridinium halide group denoted by $R_5$, there may be exemplified pyridinium chloride or pyridinium bromide group, and as quinolinium halide group, qunolinium chloride or qunolinium bromide group.

The reaction of the derivative (VII) with the tertiary amine may be carried out in the presence or absence of a solvent such as methylene chloride, chloroform, ethylene dichloride, etc. The reaction may generally be conducted at 0° to 100° C. for 5 minutes to 5 hours. When pyridine is used as the tertiary amine, the reaction may ordinally be completed by refluxing the derivative (VII) with pyridine for 1 to 5 hours.

The novel porphyrin derivatives thus obtained may be purified from the reaction mixture by a usual method, for example, extraction with a suitable solvent, recrystallization, column chromatography, etc.

The compounds of present invention have the following characteristic features effective in diagnosing and treating cancer;

1. Generating fluorescence under the irradiation of light,

2. Generating singlet oxygen ($'O_2$) under irradiation of light in the presence of oxygen (The generated $'O_2$ has cell-cidal effect), and 3. Exhibiting marked accumulation at cancer tissue as compared with normal tissue.

Namely, when the present compound selectively accumulates at cancer tissue after administration to cancer-bearing living body, the cancer tissue markedly generates fluorescence by light irradiation. Therefore, the position and size of the cancer can be ascertained by determining the fluorescence. Thus, if the position and size is ascertained, then, by irradiating the light of an appropriate wave length on the position, $'O_2$ generates at the cancer tissue which can be necrotized by the $'O_2$. The present compound rarely accumulates in a normal tissue surrounding the cancer, therefore, there is no $'O_2$ generation nor damage at the normal tissue. In such manner, cancer tissue can be selectively necrotized, which is effective in cancer treatment.

Various ways may be employed for administrating the present compound. For example, it can be administered intravenenously, subcutaneously, intraperitoneally, orally or intrarectally.

As for dosage, it may be administered at a dose of 1-350 mg/kg.

When administered intravenously, the present compound accumulates into a normal tissue such as muscle, intestine, stomach, liver, kidney, heart, brain, etc. and reaches to the maximum within several hours and thereafter it is excluded by process of time. However, in the case of cancer tissue, the accumulation reaches to the maximum within several hours and the compound still remains 24 to 72 hours after the administration. Thus selective accumulation of the compound at cancer tissue as compared with normal tissue is observed in the hours above-mentioned. Therefore, the diagnosis and treatment of cancer under irradiation of light is effective, when it is carried out in the above-mentioned hours.

In the case of the diagnosis, a light having a short wave length, about 400 nm, may be employed. In the case of the treatment, a light having a long wave length, usually about 620 nm, being well penetrable into tissue may be employed in order to allow the light to reach deeply into the cancer tissue.

The source of the light is not particularly limited, however, it is preferable to use a laser light for irradiating a localized position so as to irradiate high energy to the cancer and not to irradiate the peripheric portion of the cancer.

The present invention is further explained by Reference examples and Examples in the following:

REFERENCE EXAMPLE 1

Synthesis of 7,12-diethenyl-3,8,13,17-tetramethyl-21H,23H-porphin-2,18-dipropionic acid chloride 1 Gram of 7,12-diethenyl-3,8,13,17-tetramethyl-21H,23H-porphin-2,18-dipropionic acid is suspended in 35 ml of methylene chloride and 2.5 ml of oxalyl chloride is added dropwise thereto under refluxing. After further refluxing for 15 minutes, solvent is distilled off from the mixture under reduced pressure to give 1.1 g of 7,12-diethenyl-3,8,13,17-tetramethyl-21H,23H-porphin-2,18-dipropionic acid chloride as the residue.

EXAMPLE 1

Synthesis of 7,12-diethenyl-3,8,13,17-tetramethyl 2,18-bis [2-(dimethylaminoethyloxy)carbonylethyl]-21H,23H-porphin 1.1 Gram of 7,12-diethenyl-3,8,13,17-tetramethyl-21H,23H-porphin-2,18-dipropionic acid chloride is added to 60 ml of methylene chloride and the mixture is refluxed under addition of 5 ml of 2-dimethylaminoethanol for 45 minutes, followed by further refluxing under addition of 5 ml of 2-dimethylaminoethanol for 45 minutes. Solvent is removed from the reaction mixture under reduced pressure to give residue. The residue is dissolved in 100 ml of chloroform, washed with 100 ml of water and the chloroform layer is concentrated under reduced pressure to dryness. The resultant is purified with column chromatography packed with 100 g of alumina (activity V) using chloroform as a solvent. This procedure gives 850 mg of 7,12-diethenyl-3,8,13,17-tetramethyl-2,18-bis[2-(2-dimethylaminoethyloxy)carbonylethyl]-21H,23H-porphin as brownish black crystals melting at 187°–191° C.

Electronic spectrum ($\lambda$max, chloroform): 407, 506, 541, 577, 630 (nm)

IR spectrum (KBr): 3305, 2960, 2940, 2900, 2850, 2810, 2760, 1735 (cm$^{-1}$)

NMR spectrum (CDCl$_3$) $\delta$; 9.70, 9.56, 9.49 (s, 2H, 1H, 1H) 8.10–7.72, (m, 2H), 6.24–5.92 (m, 4H), 4.26 (t, 4H), 4.15 (t, 4H), 3.44, 3.38, 3.36, 3.34 (s, 3Hx4) 3.19 (t, 4H), 2.36 (t, 4H), 2.06 (s, 12H), 31 4.48 (s, 2H)

EXAMPLE 2

Synthesis of 7,12-diethenyl-3,8,13,17-tetramethyl-2,18-bis [2-(1,3-bis(dimethylamino)-2-propyloxy)-carbonylethyl]-21H,23H-porphin According to the process of Example 1, 1.1 g of 7,12-diethenyl-3,8,13,17-tetramethyl-21H,23H-porphin-2,18-dipropionic acid chloride is condensed with 5 ml of 1,3-bis(dimethylamino)-2-propanol to give 480 mg of 7,12-diethenyl-3,8,13,17-tetramethyl-2,18-bis[2-(1,3-bis(dimethylamino)-2-propyloxy)carbonylethyl]-21H,23H-porphin as brownish black substance melting at 181°–190° C.

Electronic spectrum ($\lambda$max, chloroform): 407.5, 505.5, 541, 576, 630.5 (nm)

IR spectrum (KBr): 3305, 2960, 2930, 2900, 2850, 2810, 2760, 1730 (cm$^{-1}$)

NMR spectrum (CDCl$_3$): $\delta$; 9.79, 9.76, 9.62, 9.56 (s, 1Hx4) 8.14–7.76 (m, 2H), 6.24–5.92 (m, 4H), 5.13 (t, 2H), 4.32 (t, 4H), 3.48, 3.44, 3.39 (s, 3H, 3H, 6H), 3.21 (t, 4H), 2.21 (d, 8H), 2.04 (s, 24H), −4.32 (s, 2H)

EXAMPLE 3

Synthesis of 7,12-diethenyl-13,8,13,17-tetramethyl-2,18-bis[2-(6-dimethylamino-1-hexyloxy)carbonylethyl]-21H,23H-porphin According to the process in Example 1, 1.1 g of 7,12-diethenyl-3,8,13,17-tetramethyl-21H,23H-porphin-2,18-dipropionic acid chloride is condensed with 5 ml of 6-dimethylamino-1-hexanol to give 450 mg of 7,12-diethenyl-3,8,13,17-tetramethyl-2,18-bis[2-(6-dimethylamino-1-hexyloxy)carbonylethyl]-21H,23H-porphin as brownish black crystals melting at 160° to 165° C.

Electronic spectrum ($\lambda$max, CHC$_{13}$): 407.5, 505.5, 541, 576, 630.5 (nm)

IR spectrum (KBr): 3300, 2920, 2850, 2800, 2750, 1735 (cm$^{-1}$)

NMR spectrum (CDCl$_3$): $\delta$; 9.7, 9.6, 9.52 (s, 2H, 1H), 8.2–7.7 (broad, 2H), 6.28–5.9 (m, 4H), 4.27 (t, 4H), 4.02 (t, 4H), 3.42, 3.38 (s, 6H, 6H), 3.16 (t, 4H), 2.02 (s, 12H), 2–1.8 (m, 4H), 1.5–1.2 (m, 4H), 1.2–0.9 (m, 16H), −4.6 (broad, 2H)

EXAMPLE 4

Synthesis of 7,12-diethenyl-3,8,13,17-tetramethyl-2,18bis[2-(N-(2-dimethylaminoethyl)carbamoyl)ethyl]-21H,23H-porphin According to the process of Example 1, 1.1 g of 7,12-diethenyl-3,8,13,17-tetramethyl-21H,23H-porphin-2,18-dipropionic acid chloride is condensed with 5 ml of 2-dimethylaminoethylamine to give 740 mg of 7,12-diethenyl-3,8,13,17-tetramethyl-2,18-bis[2-(N-(2-dimethylaminoethyl)carbamoyl)ethyl]-21H,23H-porphin as brownish black crystals melting at 300° C. or higher.

Electronic spectrum ($\lambda$max, chloroform): 406.5, 506, 541, 576, 630 (nm)

IR spectrum (KBr): 3290, 2925, 2850, 2805, 2750, 1640 (cm$^{-1}$)

NMR spectrum (CDCl$_3$): $\delta$; 9.44, 9.39, 9.34, 9.19 (s, 1Hx4) 8.06–7.62 (m, 2H), 6.8–6 6 (m, 2H), 6.21–5.88 (m, 4H), 4.02 (broad, 4H), 3.28, 3.26, 3.24, 3.15, (s, 3Hx4), 3.04–2.76 (m, 4Hx2), 1.76, 1.73 (t, 2Hx2), 1.57, 1.53 (s, 6Hx2), −5.05 (s, 2H)

EXAMPLE 5

Synthesis of 7,12-diethenyl-3,8,13,17-tetramethyl-2,18bis[2-(N-(3-dimethylaminopropyl)carbamoyl)ethyl]-21H,23H-porphin According to the process of Example 1, 1.1 g of 7,12-diethenyl-3,8,13,17-tetramethyl-21H,23H-porphin-2,18-dipropionic acid chloride is condensed with 5 ml of 3-dimethylaminopropylamine to give 650 mg of 7,12-diethenyl-3,8,13,17-tetramethyl-2,18-bis[2-N-(3-dimethylaminopropyl)carbamoyl)ethyl]-21H,23H-porphin as brownish black crystals melting at 300° C. or hihger.

Electronic spectrum ($\lambda$max, chloroform): 407, 505.5, 541, 576, 630 (nm)

IR spectrum (KBr): 3300, 3075, 2920, 2850, 2800, 2750, 1640 (cm$^{-1}$)

NMR spectrum (CDCl$_3$): $\delta$; 9.53, 9.39, 9.28 (s, 2H, 1H, 1H), 8.09–7.65 (m, 2H), 7.55–7.35 (m, 2H), 6.23–5.88 (m, 4H), 4.05 (t, 4H), 3.33, 3.28, 3.27, 3.12 (s, 3Hx4), 2.92 (t, 4H), 2.85 (t, 4H), 1.66–1.5 (t, 4H) 1.63, 1.59 (s, 6Hx2), 1.11 (q, 4H), −4.88 (s, 2H)

REFERENCE EXAMPLE 2

Synthesis of 3,8,13,17-tetramethyl-21H,23H-porphin-2,18-dipropionic acid chloride 1 Gram of 3,8,13,17-tetramethyl-21H,23H-porphin-2,18-dipropionic acid is suspended in 35 ml of methylene chloride, and 2.5 ml of oxalyl chloride is dropwise added thereto under refluxing, followed by refluxing for further 15 minutes whereby the reaction is completed. Solvent in the reaction mixture is removed under reduced pressure to give, as the residue, 1.1 g of 3,8,13,17-tetramethyl-21H,23H-porphin-2,18-dipropionic acid chloride.

EXAMPLE 6

Synthesis of
3,8,13,17-tetramethyl-2,18-bis[2-(2-dimethylaminoethyloxy)carbonylethyl]-21H,23H-porphin 1.1 Gram of 3,8,13,17-tetramethyl-21H,23H-porphin-2,18-dipropionic acid chloride is added to 60 ml of methylene chloride, and the mixture is refluxed under addition of 5 ml of 2-dimethylaminoethanol for 45 minutes, followed by refluxing under addition of further 5 ml of 2-dimethylaminoethanol for another 45 minutes. Solvent is removed from the reaction mixture under reduced pressure, and the residue is dissolved in 100 ml of chloroform, washed with 100 ml of water, and the chloroform layer is concentrated to dryness under reduced pressure. The residue thus obtained is purified with column chromatography packed with 100 g of alumina (activity V) with the use of chloroform as solvent to give 330 mg of 3,8,13,17-tetramethyl-2,18-bis[2-(2-dimethylaminoethyloxy)carbonylethyl]-21H,23H-porphin as brownish balck crystal melting at 159°–160° C.

Electronic spectrum ($\lambda$max, chloroform): 399, 496.5, 529.5, 566, 591.5, 619 (nm)

IR spectrum (KBr): 3300, 2925, 2845, 2805, 2755, 1735 (cm$^{-1}$)

NMR spectrum (CDCl$_3$): 6; 9.77, 9.68, 9.67 (s,1H, 1H, 2H), 8.76, 8.75 (s, 1Hx2), 4.25 (t, 4H), 4.12 (t, 4H), 3 56, 3.48, 3.44, 3.39 (s, 3Hx4), 3.10 (t, 4H), 2.32 (t, 4H), 2.04 (s, 6H), −4.31 (s, 2H)

REFERENCE EXAMPLE 3

Synthesis of
7,12-diethyl-3,8,13,17-tetramethyl-21H,23H-porphin-2,18-dipropionic acid chloride 1 Gram of 7,12-diethyl-3,8,13,17-tetramethyl-21H,23H-porphin-2,18-dipropionic acid is suspended in 35 ml of methylene chloride, and 2.5 ml of oxalyl chloride is dropwise added thereto under refluxing, followed by refluxing for a further 15 minutes, whereby the reaction is completed. The reaction mixture is subjected to distillation under reduced pressure to remove the solvent, whereby there is obtained, as the residue, 1.1 g of 7,12-diethyl-3,8,13,17-tetramethyl-21H,23H-porphin-2,18-dipropionic acid chloride.

EXAMPLE 7

Synthesis of
7,12-diethyl-3,8,13,17-tetramethyl-2,18-bis[2-(2-dimethylaminoethyloxy)carbonylethyl]-21H,23H-porphin 60 Milliliters of methylene chloride is added to 1.1 g of 7,12-diethyl-3,8,13,17-tetramethyl-21H,23H-porphin-2,18-dipropionic acid chloride, and 5 ml of 2-dimethylaminoethanol is added thereto under refluxing, followed by keeping the reflux for 45 minutes, and further refluxed after addition of another 5 ml of 2-dimethylaminoethanol for 45 minutes. Solvent is removed from the mixture under reduced pressure, and the resulting residue is dissolved in 100 ml of chloroform and washed with water. The chloroform layer is concentrated to dryness under reduced pressure and the resultant residue is purified with column chromatography packed with alumina (activity V) with the use of chloroform as solvent. This procedure gives 930 mg of 7,12-diethyl-3,8,13,17-tetramethyl-2,18-bis[2(2-dimethylaminoethyloxy)carbonylethyl]-21H,23H-porphin as brownish black crystal melting at 168°–172° C.

Electronic spectrum ($\lambda$max, chloroform): 399.5, 498, 532, 567, 593.5, 620.5 (nm)

IR spectrum (KBr):
3305, 2955, 2930, 2855, 2810, 2710, 1735 (cm$^{-1}$)

NMR spectrum (CDCl$_3$): $\delta$; 9.92, 9.87, 9.83, 9.81 (s, 1Hx4), 4.35,, 4.32 (t, 2Hx2), 4.13 (t, 4H), 3.94, 3.91 (q, 2Hx2), 3.56, 3.50, 3.44 (s, 3H, 6H, 3H), 3.25 (t, 4H), 2.33 (t, 4H), 2.02 (s, 6H), 1.78, 1.77 (t, 2Hx2), −3.92 (s, 2H)

EXAMPLE 8

Synthesis of
7,12-diethenyl-3,8,13,17-tetramethyl-2,18-bis[2-(2-trimethylammonioethyloxy)carbonylethyl]-21H,23H-porphin diiodide 100 Milligrams of 7,12-diethenyl-3,8,13,17-tetramethyl-2,18-bis[2-(2-dimethylaminoethyloxy)carbonylethyl]-21H,23H-porphin obtained in Example 1 is dissolved in 10 ml of methylene chloride, and 1 ml of methyl iodide is added thereto and the precipitated crystals are recovered by filtration to give 126 mg of 7,12-diethenyl-3,8,13,17-tetramethyl-2,18-bis[2-(2-trimethylammonioethyloxy)carbonylethyl]-21H,23H-porphin diiodide as brownish black crystals.

Electronic spectrum ($\lambda$max, water): 376, 512, 548, 576.5, 630.5 (nm)

IR spectrum (KBr): 3300, 2900, 1725 (cm$^{-1}$)

NMR spectrum (DMSO-d$_6$) $\delta$; 9.74, 9.66 (s, 2Hx2), 8.4–7.8 (m, 2H), 6.4–6.0 (m, 4H), 4.5–4.0 (broad, 4Hx2), 3.48 (s, 3Hx4), 3.26 (broad, 4Hx2), 2.79 (s, 18H), −5.08 (broad, 2H)

EXAMPLE 9

Synthesis of
7,12-diethenyl-3,8,13,17-tetramethyl-2,18-bis[2-(1,3-bis(trimethylammonio)-2-propyloxy)carbonylethyl]-21H,23H-porphin tetraiodide 100 Milligrams of 7,12-diethenyl-3,8,13,17-tetramethyl-2,18-bis[2-(1,3-bis(dimethylamino)-2-propyloxy)carbonylethyl]-21H,23H-porphin obtained in Example 2 is dissolved in 10 ml of methylene chloride, and 1 ml of methyl iodie is added thereto and the precipitated crystals are recovered by filtration to give 100 mg of 7,12-diethenyl-3,8,13,17-tetramethyl-2,18-bis[2-(1,3-bis(trimethylammonio-2-propyloxy)carbonylethyl)-21H,23H-porphin tetraiodide as brownish black crystals.

Electronic spectrum ($\lambda$max, water): 398, 509, 543.5, 573.5, 628.5 (nm)

IR spectrum (KBr): 3300, 2995, 2930, 2850, 1740 (cm$^{-1}$)

NMR spectrum (DMSO-d$_6$): 10.20–9.96 (s, 1Hx4), 8.52–8.02 (m, 2H), 6.44–6.06 (m, 4H), 5.88–5.58 (broad, 2H), 4.68–4.28 (broad, 4H), 3.96–3.4 (m, 4H, 4H, 4H), 3.64–3.56 (s, 3Hx4), 3.08 (s, 36H), −4.26 (broad, 2H)

EXAMPLE 10

Synthesis of
7,12-diethenyl-3,8,13,17-tetramethyl-2,18-bis[2-(N-(2-trimethylammonioethyl)carbamoyl)ethyl]-21H,23H-porphin diiodide 100 Milligrams of 7,12-diethenyl-3,8,13,17-tetramethyl-2,18-bis[2-(N-(2-dimethylaminoethyl)carbamoyl)ethyl]-21H,23H-porphin obtained in Example 4 is dissolved in 20 ml of methylene chloride under heating. After cooling the mixture to room temperature, 1 ml of methyl iodide is added thereto, and the precipitated crystals are recovered by filtration to give 127 mg of 7,12-diethenyl-3,8,13,17-tetramethyl-2,18-bis[2-(N-(2-trimethylammonioethyl)carbamoyl)ethyl]-21H,23H-porphin diiodide as brownish black crystals.

Electronic spectrum (λmax, water): 377.5, 510, 548, 575.5, 630 (nm)

IR specrum (KBr): 3300, 3230, 2995, 2900, 2845, 1655 (cm$^{-1}$)

NMR spectrum (in DMSO-d$_6$): δ; 10.2-10.05 (s, 1Hx4), 8.6-8.0 (m, 2H), 6.6-6.0 (m, 4H), 4.37 (t, 4H), 3.8-3.6 (m, 8H), 3.28 (broad, 3Hx4), 3.14 (t, 4H), 2.54 (s, 18H)

EXAMPLE 11

Synthesis of 7,12-diethenyl-3,8,13,17-tetramethyl-2,18-bis[2-(N-(3-trimethylammoniopropyl)carbamoyl)ethyl]-21H,23H-porphin diiodide 100 Milligrams of 7,12-diethenyl-3,8,13,17-tetramethyl-2,18-bis[2-(N-(3-diethylaminopropyl)carbamoyl)ethyl]-21H,23H-porphin is dissolved in 10 ml of methylene chloride, and 1 ml of methyl iodide is added thereto. The precipitated crystals are recovered by filtration to give 126 mg of 7,12-diethenyl-3,8,13,17-tetramethyl-2,18-bis[2-(N-(3-trimethylammoniopropyl)-carbamoyl)ethyl]-21H,23H-porphin diiodide as brownish black crystals.

Electronic spectrum (λmax, water):
380.5, 510, 546, 577, 631 (nm)

IR spectrum (KBr):
3300, 3250, 2900, 2850, 1640 (cm$^{-1}$)

NMR spectrum (DMSO-d$_6$): δ; 9.94, 9.86, 9.78 (s, 1H, 1H, 2H), 8.5-8.06 (m, 2H), 8.02-7.86 (m, 2H), 6.4-6.09 (m, 4H), 4.3 (broad, 4H), 3.54 (broad, 12H), 3.1-2.8 (broad, 8H), 0.62 (broad, 4H), 1.3 (broad, 4H), -4.9 (broad, 2H)

REFERENCE EXAMPLE 4

Affinity to cancer cells

1×10$^7$ MKSA cells originated from mouse nephradenoma were transplanted on the back of 3-week-aged Balb/c mouse, and after 2-3 weeks, the present porphin derivative is intravenously administered to the tail of the mouse at a dose of 20 mg/kg body weight. After 24 hours from the administration, organs and cancer cells were excised from the mouse, and fluorescence generated from them, which was originated from the porphin derivative, was measured on each of them by using laser diagnosis apparatus (K. Aizawa et al., LASER IGAKU KAISHI, Vol. 5, pp. 63-68, (1984)). The results are summarized to strength of the fluorescence at cancer tissue and strength ratio of the fluorescence at normal tissues to the fluorescence at cancer tissue in Table 1.

In the Table, respective [8] and [10] denote the compounds obtained in Examples 8 and 10, Hp denotes hematoporphyrin and HpD denotes the prophyrine derivative obtained by the procedure described in Porphyrin Localization and Treatment of Tumors, pp. 75-78, (1984).

TABLE 1

| Compound | Strength of fluorescence at cancer | Strength ratio of fluorescence (normal organs/cancer) | | | |
|---|---|---|---|---|---|
| | | Skin | Lung | Liver | Kidney |
| [8] | 15.08 | 0.47 | 0.01 | 0.09 | 0.00 |
| [10] | 14.89 | 0.74 | 0.07 | 0.04 | 0.00 |
| HpD | 5.70 | 0.84 | 0.01 | 0.09 | 0.00 |
| Hp | 3.45 | — | 0.45 | 0.45 | 0.45 |

REFERENCE EXAMPLE 5

Therapeutic effect

1×10$^7$ MKSA cells originated from mouse nephradenoma were transplanted on the back of 3-week-aged Balb/c mouse, and at the stage when the tumor had grown up to have diameter of about 1 cm after 2 to 3 weeks, the compound obtained in Example 8 was intraveneously administered to the tail of the mouse at a dose of 20 mg/kg body weight. At 24 hours after the administration, the hair on the tumor was taken off to lay the skin bare, and excimer laser (wave length 625 nm) was irradiated, whereby the tumor disappeared after 3 days.

REFERENCE EXAMPLE 6

Synthesis of 7,12-diethyl-3,8,13,17-tetramethyl-2,18-bis(3-bromopropyl)-21H,23H-porphin To 1 liter of methylene chloride, 50 ml of dimethylformamide is added and the mixture is agitated, followed by addition of 25 ml of thionyl bromide, 60 g of potassium carbonate and 2.5 g of 7,12-diethyl-3,8,13,17-tetramethyl-2,18-bis(3-hydroxypropyl)-21H,23H-porphin. The mixture is stirred at room temperature for 5 hours. The reaction solution is poured on 1 kg of ice to decompose excess thionyl bromide and the mixture is subjected to layer separation. The methylene chloride layer is washed with each 100 ml of water three times, dried on anhydrous magnesium sulfate and subjected to distillation under reduced pressure to give 4.5 g of crude product. The crude product is washed with 30 ml of methanol, dried and purified with column chromatography packed with alumina (activity V) in an amount of 200 g with the use of methylene chloride as solvent, whereby 2.7 g (yield 87.4%) of the desired compound is obtained as dark reddish brown substance.

Melting point: 300° C. or higher

Electronic spectrum (λmax, DMF): 620.5, 566.3, 529.5, 496.7, 396.0 (nm)

IR spectrum (KBr): 3320, 2950, 2920, 2850, 835, 740 (cm

NMR spectrum (CDCl$_3$): δ; -3.78 (2H, s), 1.82 (6H, t), 2.70 (4H, t), 3.48-3.68 (16H, m), 4.02 (8H, m), 9.80 (1H, s), 9.83 (3H, s)

EXAMPLE 13

Synthesis of 7,12-diethyl-3,8,13,17-tetramethyl-2,18-bis(3-pyridiniopropyl)-21H,23H-porphin dibromide To 100 mg of 7,12-diethyl-3,8,13,17-tetramethyl-2,18-bis(3-bromopropyl)-21H,23H-porphin, 2 ml of pyridine is added, followed by refluxing for 5 hours. The precipitated crystals are recovered by filtration, washed with 3 ml of pyridine and dried, whereby 100 mg (yield 81.1%) of dark reddish brown desired compound is obtained.

Melting point: 300° C. or higher

Electronic spectrum (λmax, DMF): 620.5, 566.5, 529.5, 497.0, 397.5 (nm)

IR spectrum (KBr): 3300, 3000, 2960, 2930, 2850, 1630, 1480, 835, 740, 675 (cm$^{-1}$)

NMR specrum (DMSO-d$_6$): δ; −3.96 (2H, s), 1.74 (6H, t), 2.85 (4H, broad), 3.20 (12H, s), 3.96 (4H, broad), 4.30 (4H, broad), 5.30 (4H, broad), 8.02 (4H, t), 8.42 (2H, t), 9.36 (4H, d), 9.86 (1H, s), 9.90 (3H, s)

EXAMPLE 14

Synthesis of 3,8,13,17-tetramethyl-2,18-bis(3-pyridiniopropyl)-21H,23H-porphin dibromide To 120 mg of 3,8,13,17-tetramethyl-2,18-bis(3-bromopropyl)-21H,23H-porphin, 2 ml of pyridine is added, followed by refluxing for 5 hours. The precipitated crystals are recovered by filtration, washed with 3 ml of pyridine and dried, whereby 140 mg (yield 92.8%) of brownish black desired compound is obtained.

Melting point: 300° C. or higher

Electronic spectrum (λmax, DMF): 623.3, 568.9, 533.3, 500.1, 401.0 (nm)

IR spectrum (KBr): 3300, 3000, 2950, 2900, 2850, 1630, 1480, 835, 720, 675 (cm$^{-1}$)

NMR spectrum (DMSO-d$_6$): δ; 2.74 (4H, broad), 3.30 (12H, s), 4.20 (4H, broad), 5.24 (4H, broad), 8.04 (6H, broad), 8.44 (2H, broad), 8.80–9.40 (8H, m)

EXAMPLE 15

Synthesis of 7,12-diethenyl-3,8,13,17-tetramethyl-2,18-bis(3-pyridiniopropyl)-21H,23H-porphin dibromide To 100 mg of 7,12-diethenyl-3,8,13,17-tetramethyl-2,18-bis(3-bromopropyl)-21H,23H-porphin, 2 ml of pyridine is added, followed by refluxing for 5 hours. The precipitated crystals are recovered by filtration, washed with 3 ml of pyridine and dried, whereby 116 mg (yield 94.5 of brownish black desired compound is obtained.

Melting point: 300° C. or higher

Electronic spectrum (λmax, DMF): 632.0, 576.8, 542.0, 506.5, 409.0 (nm)

IR spectrum (KBr): 3300, 3000, 2900, 2850, 1625, 1480, 835, 725, 680 (cm$^{-1}$)

REFERENCE EXAMPLE 7

Affinity to cancer cells $1 \times 10^7$ MKSA cells originated from mouse nephradenoma are transplanted on the back of 3-week-aged Balb/c mouse, and after 2–3 weeks, the porphin derivative obtained by the present invention is intraveneously administered to the tail of the mouse at a dose of 20 mg/kg body weight. After 24 hours, organs and cancer tissue are taken out and fluorescence generated from them, which is originated from the prophin derivative, is measured on each of them by using laser diagnosis apparatus (K. Aizawa et al., LASER IGAKU KAISHI, Vol. 5, pp. 63–68, (1984)). The results are summarized to the fluorescence strength at cancer tissue and the ratio of the fluorescence strength at normal tissue to that at cancer tissue in Table 2. In the Table, [13] denotes the product compound in Example 13, Hp denotes hematoporphyrin and HpD denotes the porphyrin derivative obtained by the procedure described in Porphyrin Localization and Treatment of Tumors, pp. 75–78, (1984).

TABLE 2

| Compound | Strength of fluorescence at cancer | Strength ratio of fluorescence (normal organs/cancer) | | | |
|---|---|---|---|---|---|
| | | Skin | Lung | Liver | Kidney |
| [13] | 16.36 | — | 0.01 | 0.06 | 0.01 |
| HpD | 5.70 | 0.84 | 0.01 | 0.09 | 0.00 |
| Hp | 3.45 | — | 0.45 | 0.45 | 0.45 |

EXAMPLE 16

Synthesis of 7,12-bis(2-pyridinioethyl)-3,8,13,17-tetramethyl-2,18-bis(2-methoxycarbonylethyl)-21H,23H-porphin dibromide To 500 mg of 7,12-bis(2-bromoethyl)-3,8,13,17-tetramethyl-21H,23H-porphin-2,18-dipropionic acid methyl ester, 10 ml of pyridine is added, followed by refluxing for 5 hours. The precipitated crystals are recovered by filtration, washed with 5 ml of pyridine and dried, whereby 550 mg (yield 99.5%) of dark reddish desired compound is obtained.

Electronic spectrum (λmax, PBS): 621.5, 569, 543, 508, 370.5 (nm)

IR spectrum (KBr): 3425, 3325, 3050, 2950, 2850, 1730, 1630, 1485, 1460, 1440, 1270, 1220, 1200, 1165, 1100, 840, 740, 680 (cm$^{-1}$)

EXAMPLE 17

Synthesis of 7,12-bis(2-quinolinioethyl)-3,8,13,17-tetramethyl-2,18-bis(2-methoxycarbonylethyl)-21H,23H-porphin dibromide To 100 mg of 7,12-bis(2-bromoethyl)-3,8,13,17-tetramethyl-21H,23H-porphin-2,18-dipropionic acid methyl ester, 2 ml of quinoline is added, followed by refluxing for 5 hours. To the resultant, 20 ml of hexane is added, and the precipitated crystals are recovered by filtration, washed with 5 ml of hexane and dried, whereby 135 mg (yield 99.6%) of dark reddish desired compound is obtained.

IR spectrum (KBr): 3400, 3300, 2920, 2850, 1725, 1590, 1520, 1430, 1395, 1365, 1255, 1225, 1195, 1160, 1110, 830, 760, 740 (cm$^{-1}$)

$^{13}$C NMR spectrum (CD30D): 173.8, 148.6, 146.9, 143.8, 142.5, 139.3, 139.1, 138.3, 136.9, 136.6, 136.0, 132.0, 130.8, 130.4, 129.0, 128.3, 126.7, 125.1, 120.8, 118.0, 96.8, 95.4, 36.7, 21.2, 11.2, 10.2, 10.9, 10.6 (ppm)

EXAMPLE 18

Synthesis of 7,12-bis(2-quinolinioethyl)-3,8,13,17-tetramethyl-2,18-bis-(2-carboxyethyl)-21H,23H-porphin dibromide To 100 mg of 7,12-bis(2-bromoethyl)-3,8,13,17-tetramethyl-21H,23H-porphin-2,18-dipropionic acid, 2 ml of quinoline is added, followed by refluxing for 5 hours. To the resultant, 20 ml of hexane is added, and the precipitated crystals are recovered by filtration, washed with 5 ml of hexane and dried, whereby 110 mg (yield 95.5%) of desired compound is obtained in dark reddish brown colour.

IR spectrum (KBr): 3400, 3100, 2920, 2850, 1720, 1630, 1590, 1525, 1455, 1380, 1225, 1160, 1105, 815, 770, 740 (cm$^{-1}$)

REFERENCE EXAMPLE 8
Affinity to cancer cells $1 \times 10^7$ MKSA cells originated from mouse nephradenoma are transplanted on the back of 3-week-aged Balb/c mouse, and after 2 to 3 weeks, the porphin derivative obtained by the present invention is intravenously administered to the tail of the mouse at a dose of 20 mg/kg body weight. After 24 hours, organs and cancer tissue are taken out and fluorescence generated from them, which is originated from the porphin derivative, are measured on each of them by using laser diagnosis apparatus (K. Aizawa et al., LASER IGAKU KAISHI, Vol. 5, pp. 63–68, (1984)). The results are shown in Table 3 as strength of the fluorescence at cancer tissue and the ratio of fluorescence strength at normal tissue to that at cancer tissue. In the Table, [16] denotes the product compound in Example 16, Hp denotes hematoporphirin and HpD denotes the porphyrin derivative obtained by the procedure described in Porphyrin Localization and Treatment of Tumors, pp. 75–78, (1984).

TABLE 3

| Compound | Strength of fluorescence at cancer | Strength ratio of fluorescence (normal organs/cancer) | | | |
|---|---|---|---|---|---|
| | | Skin | Lung | Liver | Kidney |
| [16] | 3.00 | 0.00 | 0.00 | 0.00 | 0.00 |
| HpD | 5.70 | 0.84 | 0.01 | 0.09 | 0.00 |
| Hp | 3.45 | — | 0.45 | 0.45 | 0.45 |

We claim:

1. A porphyrin derivative of the general formula:

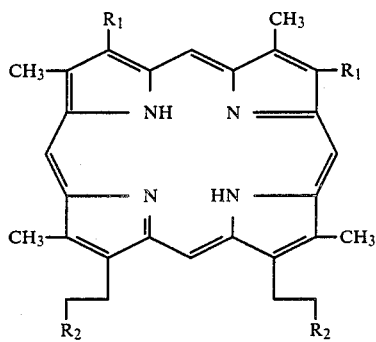

wherein $R_1$ each independently denotes a hydrogen, a $C_1$-$C_4$ alkyl group or an ethenyl group, and $R_2$ each independently denotes $COZ(C_mH_{2m})Q$, $COZCH(C_mH_{2m}Q)_2$, $-CH_2-Q$ [wherein Z is O, S or NH, m is an integer of 1 to 23, and Q is a di-($C_1$-$C_4$ alkyl)amino group or tri-($C_1$-$C_4$ alkyl)ammonium halide group] or

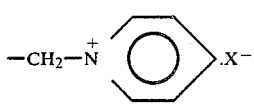

(wherein X is a halogen); or $R_1$ each independently denotes $-C_2H_4-Q$ (wherein Q is the same as defined above),

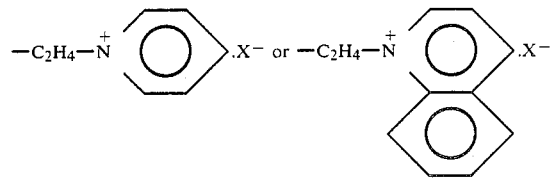

(wherein X is the same as defined above), and $R_2$ each independently denotes a carboxyl group or a $C_1$-$C_4$ alkoxycarbonyl group.

2. A porphyrin derivative as claimed in claim 1, which is represented by the formula;

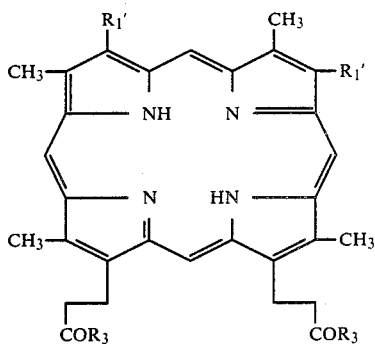

wherein each $R_1'$ is a hydrogen, a $C_1$-$C_4$ alkyl group or an ethenyl group, and each $R_3$ is $O(C_mH_{2m})Q$, $OCH(CH_2Q)_2$, $S(C_mH_{2m})Q$ or $NH(C_mH_{2m})Q$ wherein m and Q are the same as defined in claim 1.

3. A prophyrin derivative as claimed in claim 1, which is represented by the formula:

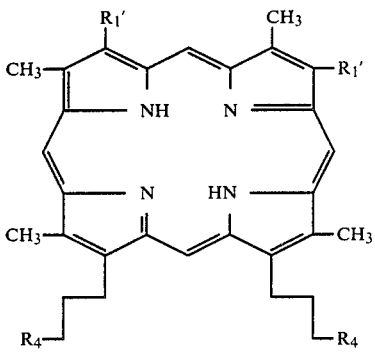

wherein each $R_1'$ is a hydrogen, a $C_1$-$C_4$ alkyl group or an ethenyl group, and each $R_4$ is a tri($C_1$-$C_4$ alkyl) ammonium halide group or pyridinium halide group.

4. A porphyrin derivative as claimed in claim 1, which is represented by the formula:

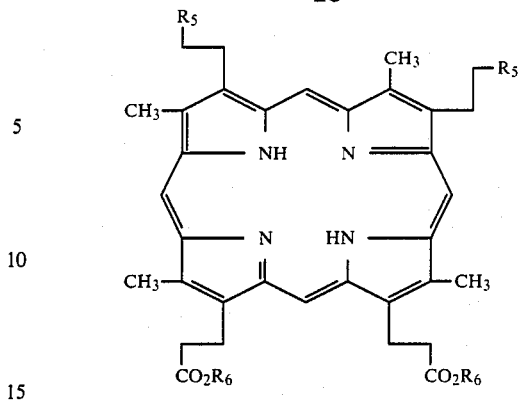

(wherein each $R_5$ is a tri-$(C_1-C_4$ alkyl)ammonium halide group, pyridinium halide group or quinolinium halide group, and each $R_6$ is a hydrogen or a $C_1-C_4$ alkyl group).

5. The porphyrin derivative of claim 1 which is 7,12-diethenyl-3,8,13,17-tetramethyl-2,18-bis[2-trimethylammonioethyloxy)carbonylethyl]-21H,23H-porphin dibromide.

6. The porphyrin derivative of claim 1 which is 7,12-diethenyl-3,8,13,17-tetramethyl-2,18-bis[2-(N-(2-trimethylammonioethyl)carbamoyl)ethyl]-21H,23H-porphin dibromide.

7. The porphyrin derivative of claim 1 which is 7,12-diethyl-3,8,13,17-tetramethyl-2,18-bis(3-pyridiniopropyl)-21H,23H-prophin dibromide.

* * * * *